United States Patent [19]

Dotson, Jr. et al.

[11] 4,328,357
[45] May 4, 1982

[54] PROCESS FOR PREPARING NITROGEN COMPOUNDS

[75] Inventors: Anderson O. Dotson, Jr., Somerset; Francis T. Wadsworth, Trenton; Lionel T. Wolford, Freehold, all of N.J.

[73] Assignee: Saytech, Inc., East Brunswick, N.J.

[21] Appl. No.: 927,807

[22] Filed: Jul. 24, 1978

Related U.S. Application Data

[62] Division of Ser. No. 759,949, Jan. 17, 1977, Pat. No. 4,140,862.

[51] Int. Cl.³ .................................... C07C 45/61
[52] U.S. Cl. ............................ 560/83; 252/609
[58] Field of Search ................................ 560/83

[56] References Cited

U.S. PATENT DOCUMENTS 4,092,345  5/1978  Wolford et al. ............... 260/501.16

OTHER PUBLICATIONS

Matsuda et al., Japanese Kokai 76 16607 as cited in Chem. Abstracts 85, 20871t (1976).
Hattori, Japanese 22, 479 (65) as cited in Chem. Abstracts 64 3757g (1966).

*Primary Examiner*—Natalie Trousof
*Assistant Examiner*—Vera C. Clarke
*Attorney, Agent, or Firm*—Donald L. Johnson; Joseph D. Odenweller; Teresa M. Stanek

[57] ABSTRACT

(Cyclo)alkylenediammonium compounds corresponding to the formula:

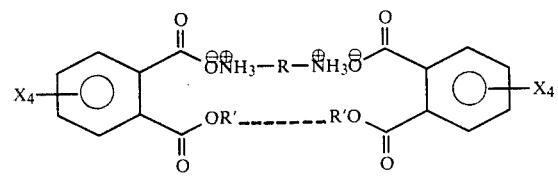

wherein X is halogen, R is an alkylene or cycloalkylene group containing 2–15 carbon atoms, each R' alone is an alkyl, cycloalkyl, or aralkyl group, and R'–R' together represent an alkylene, cycloalkylene, or aralkylene group are prepared by esterifying a tetrahalophthalic anhydride with a mono- or dihydroxyalkane, -cycloalkane, or -aralkane having a boiling point below 250° C. to form a half-ester and then reacting the half-ester with a stoichiometric amount of a diaminoalkane or diaminocycloalkane containing 2–15 carbon atoms.

The (cyclo)alkylenediammonium compounds of the invention are useful as flame retardants for normally flammable organic polymers and also have utility as intermediates for the preparation of N,N'-(cyclo)alkylene-bis-tetrahalophthalimides, which are also useful as flame retardants. The imides are prepared simply by heating the diammonium compounds.

2 Claims, No Drawings

PROCESS FOR PREPARING NITROGEN COMPOUNDS

This is a division of application Ser. No. 759,949, filed Jan. 17, 1977, now U.S. Pat. No. 4,140,862.

BACKGROUND OF THE INVENTION

1. Field of the Invention

This invention relates to novel (cyclo)alkylenediammonium salts of tetrahalophthalate half-esters and to bismimides prepared therefrom.

2. Description of the Prior Art

As taught in U.S. Pat. No. 3,873,567 (Cyba), British Pat. No. 1,287,934 (Raychem), and Sydney M. Spatz and Herman Stone, "Some N-Substituted Tetrabromophthalimide Fire-Retardant Additives," INDUSTRIAL AND ENGINEERING CHEMISTRY PRODUCT RESEARCH AND DEVELOPMENT, Volume 8, pp. 397-398 (1969), N,N'-alkylene-bis-tetrahalophthalimides having utility as flame retardants can be prepared by reacting a tetrahalophthalic anhydride with a diaminoalkane in an organic solvent medium. These processes, which produce the bisimides via an amic acid intermediate corresponding to the formula:

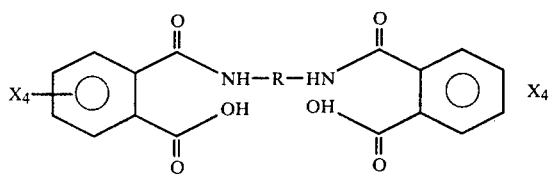

are difficult to control, present filtration problems, and are less economical than is desirable.

SUMMARY OF THE INVENTION

An object of this invention is to provide a novel process for preparing N,N''-(cyclo)alkylene-bis-tetrahalophthalimides.

Another object is to provide such a process which is economical, easily controlled, and conducive to the formation of a readily filterable product.

A further object is to provide such a process which leads to the formation of the bisimides via novel intermediates.

A still further object is to provide novel intermediates which are useful as flame retardants as well as having utility in the formation of bisimides.

These and other objects are attained by (1) esterifying a tetrahalophthalic anhydride with a mono- or dihydroxyalkane, -cycloalkane, or -aralkane having a boiling point below 250° C. to form a half-ester corresponding to the formula:

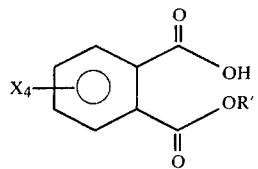

wherein X is halogen and R' is an alkyl, cycloalkyl, or aralkyl group, or a half-ester corresponding to the formula:

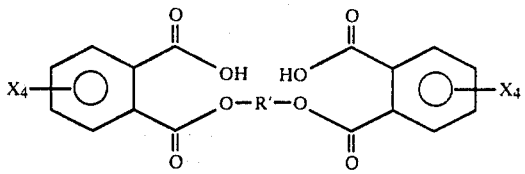

wherein X is halogen and R' is an alkylene, cycloalkylene or aralkylene group, (2) reacting the resultant half-ester with a stoichiometric amount of a diaminoalkane or diaminocycloalkane containing 2-15 carbon atoms to form an alkylene- or cycloalkylenediammonium compound corresponding to the formula:

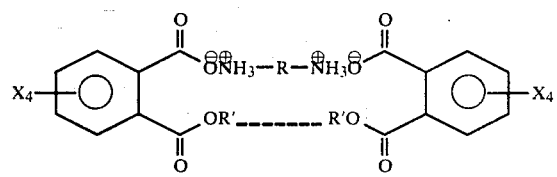

and, when a bisimide is desired, (3) recovering the diammonium compound and (4) heating it at about 125°-250° C. until it reaches constant weight, indicating the formation of an N,N'-(cyclo)alkylene-bis-tetrahalophthalimide corresponding to the formula:

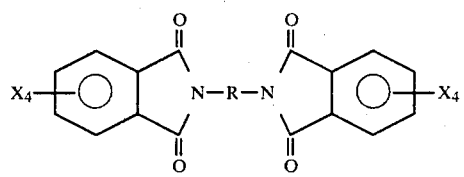

wherein X is halogen and R is an alkylene or cycloalkylene group containing 2-15 carbon atoms.

DESCRIPTION OF THE PREFERRED EMBODIMENTS

The tetrahalophthalic anhydride that is esterified in the practice of the invention is usually tetrabromophthalic anhydride, tetrachlorophthalic anhydride, or a mixture thereof; and it is preferably tetrabromophthalic anhydride.

As indicated above, the alcohol that is reacted with the tetrahalophthalic anhydride in the practice of the invention can be any mono- or dihydroxyalkane, -cycloalkane, or -aralkane having a boiling point below 250° C. However, for reasons of availability, it is preferably an alcohol containing 1-12 carbon atoms, more preferably 1-6 carbon atoms, and it is most preferably methanol or ethylene glycol. Exemplary of other alcohols that can be used are ethanol; propanol; isopropyl alcohol; the normal, secondary, tertiary, and isobutyl alcohols; the pentanols; the hexanols; the decanols; cyclohexanol; benzyl alcohol; propylene glycol; butylene glycol; cyclohexanediol; xylylene glycol, etc., and mixtures thereof.

As indicated above, the diaminoalkane or diaminocycloalkane that is used in the practice of the invention can be any such compound containing 2-15 carbon atoms. However, it is preferably a diaminoalkane containing 2-6 carbon atoms and most preferably 1,2-diaminoethane. Exemplary of other diamines that can be used are 1,2-diaminopropane, 1,3-diaminopropane, 1,4-diaminobutane, 1,5-diaminopentane, 1,6-diaminohexane, 1,2-diaminocyclohexane, 1,12-diaminododecane, 4,4'-methylene-bis-cyclohexylamine, etc.

The manner of esterifying the anhydride with the alcohol is not critical. Formation of the half-ester may be accomplished simply by contacting the reactants in a suitable reaction medium at a suitable reaction temperature, usually a temperature in the range of about 20°–200° C. and when necessary, applying superatmospheric pressure to prevent the boiling that would otherwise occur at the higher reaction temperatures. However, it is preferred to conduct the reaction at reflux temperature. Most conveniently the reaction medium is an excess of the alcohol, but it may be any inert solvent boiling above about 60° C., e.g., at about 60°–200° C. Exemplary of such solvents are benzene, xylene, toluene, chlorobenzene, chloroform, etc., and mixtures thereof. The total amount of reaction medium employed for the esterification, although not critical, is conveniently such as to provide a solids content of about 5–80%, preferably about 5–70%, and most preferably about 25–50%, by weight when the diamine is added for the subsequent step of the synthesis.

The reaction of the diamine with the half-ester is most suitably accomplished by adding the diamine to the reaction mixture resulting from the esterification reaction at a temperature in the range of about 50°–200° C., superatmospheric pressures being employable when they are desired to prevent boiling. It is advantageous to conduct the reaction at reflux temperature. It is also advantageous to conduct the reaction by adding the diamine gradually to the reaction mixture, e.g., over a period of about 0.25–4 hours, and then continuing to heat the reaction mixture for at least about 45 minutes, frequently for about 0.75–2 hours. The product may then be recovered by conventional cooling, filtering, and drying techniques.

When the diammonium compound thus obtained is desired only as an intermediate for the preparation of a bisimide, it may then be converted to the bisimide by heating it at about 125°–250° C. until it reaches constant weight. The time required for this reaction varies with the particular temperature employed but is usually in the range of about 1–48 hours, the shorter times being sufficient at the higher temperatures and the longer times sometimes being required at the lower temperatures.

The invention is advantageous in that it provides an economical and easily controlled process for preparing N,N'-(cyclo)-alkylene-bis-tetrahalophthalimides, which have known utility as flame retardants, and it is conducive to the formation of a readily filterable product. It is also advantageous in that the process leads to the formation of the bisimides via novel diammonium intermediates which are useful per se as flame retardants.

The following examples are given to illustrate the invention and are not intended as a limitation thereof.

EXAMPLE I

Part A

Charge 240 g. of methanol and 150 g. of tetrabromophthalic anhydride to a suitable reaction vessel. Heat the reaction mixture at reflux for two hours, and add a solution of 9.69 g. of 1,2-diaminoethane in 10 g. of methanol over a period of 30 minutes. Continue refluxing for an additional 90 minutes. Then cool to 25° C., filter, and air dry the product. The process results in the formation of 149 g. of ethylenediammonium-bis-methyl tetrabromophthalate, a white crystalline material. Infrared and thermogravimetric analyses support the identification of the product.

Part B

Heat the product of Part A in a vacuum oven at 136° C. for 16 hours. The process results in 99.8% conversion to N,N'-ethylene-bis-tetrabromophthalimide.

EXAMPLE II

Repeat Example I except for replacing the fresh methanol with recovered mother liquor from Example I. The ethylenediammonium-bis-methyl tetrabromophthalate is obtained in 95% yield.

EXAMPLE III

Repeat Example I except for replacing the methanol with ethylene glycol. The product of Part A is ethylenediammonium ethylene-bis-tetrabromophthalate. The product of Part B is N,N'-ethylene-bis-tetrabromophthalimide.

EXAMPLE IV

Repeat Example I except for replacing the 1,2-diaminoethane with an equimolar amount of 1,2-diaminopropane. The product of Part A is (1,2-propylene)diammonium-bis-methyl-tetrabromophthalate. The product of Part B is N,N'-(1,2-propylene)-bis-tetrabromophthalimide.

EXAMPLE V

Repeat Example I except for replacing the 1,2-diaminoethane with an equimolar amount of 1,3-diaminopropane. The product of Part A is (1,3-propylene)diammonium-bis-methyl-tetrabromophthalate. The product of Part B is N,N'-(1,3-propylene)-bis-tetrabromophthalimide.

EXAMPLE VI

Repeat Example I except for replacing the 1,2-diaminoethane with an equimolar amount of 1,6-diaminohexane. The product of Part A is hexamethylenediammonium-bis-methyl tetrabromophthalate. The product of Part B is N,N'-hexamethylene-bis-tetrabromophthalimide.

Similar results are observed when the examples are repeated except that one or more ingredients are replaced by materials taught to be their equivalents in the specification.

It is obvious that many variations can be made in the products and processes set forth above without departing from the spirit and scope of this invention.

What is claimed is:

1. A process which comprises (1) esterifying a tetrahalophthalic anhydride with a mono- or dihydroxyalkane, -cycloalkane, or -aralkane having a boiling point below 250° C. to form a half-ester corresponding to the formula

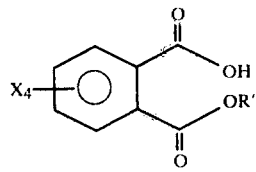

wherein X is halogen and R' is an alkyl, cycloalkyl, or aralkyl group, or a half-ester corresponding to the formula:

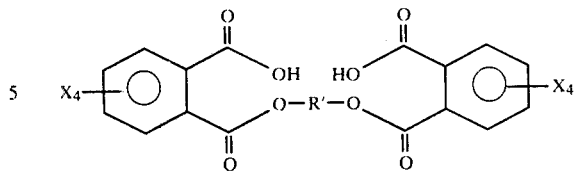

wherein X is halogen and R' is an alkylene, cycloalkene, or aralkylene group and (2) reacting the resultant half-ester with a stoichiometric amount of a diaminoalkane or diaminocycloalkane containing 2–15 carbon atoms to form an alkylene- or cycloalkylenediammonium compound corresponding to the formula:

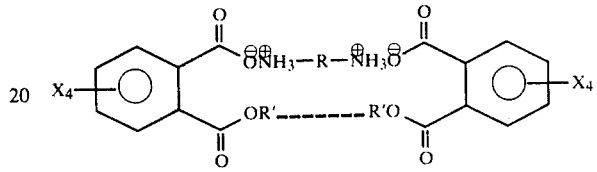

2. The process of claim 1 wherein the tetrahalophthalic anhydride is tetrabromophthalic anhydride, the alcohol is methanol, and the diaminoalkane is 1,2-diaminoethane.

* * * * *